United States Patent [19]

Nawata et al.

[11] Patent Number: 4,727,190
[45] Date of Patent: Feb. 23, 1988

[54] PROCESS FOR PREPARING BENZOPHENONE-AZINES

[75] Inventors: Takanari Nawata, Tokyo; Shuzabu Sakaguchi; Toshiaki Kohzaki, both of Ibaraki; Osamu Aoki, Chiba; Norio Takeda, Saitama; Yoshiyuki Aoki, Ibaraki; Masafumi Shimpo, Tokyo, all of Japan

[73] Assignee: Mitsubishi Gas Chemical Company, Inc., Japan

[21] Appl. No.: 918,656

[22] Filed: Oct. 14, 1986

Related U.S. Application Data

[63] Continuation of Ser. No. 702,551, Feb. 19, 1985, abandoned.

[30] Foreign Application Priority Data

Feb. 17, 1984 [JP] Japan .................................. 59-28322

[51] Int. Cl.$^4$ .......................................... C07C 109/16
[52] U.S. Cl. .................................................. 564/249
[58] Field of Search ........................................ 564/249

[56] References Cited

U.S. PATENT DOCUMENTS 2,870,206  1/1959  Meyer et al. ........................ 564/249
4,079,080  3/1978  Hayashi ............................... 564/249
4,347,383  8/1982  Isshiki et al. ........................ 564/249

FOREIGN PATENT DOCUMENTS 101617  2/1980  Japan .................................. 564/249
146019  2/1984  Japan .................................. 564/249

Primary Examiner—Donald B. Moyer
Assistant Examiner—L. Hendriksen
Attorney, Agent, or Firm—Sughrue, Mion, Zinn, Macpeak and Seas

[57] ABSTRACT

A process for continuously preparing benzophenone-azines comprising oxidizing benzophenone-imines with molecular oxygen or a molecular oxygen-containing gas in the presence of a copper halide catalyst is disclosed. The oxidation reaction is carried out in a multi-stage system under an oxygen partial pressure gradually decreasing from the former stage to the latter stage and at a conversion gradually decreasing from the former stage to the latter stage, while controlling the conversion so that the molar ratio of the benzophenone-imines to the copper halide in the final stage be maintained at 1 or more. By the process, the continuous reaction can stably be performed at a high conversion of the benzophenone-imines without involving insolubilization and sedimentation of the catalyst.

11 Claims, 1 Drawing Figure

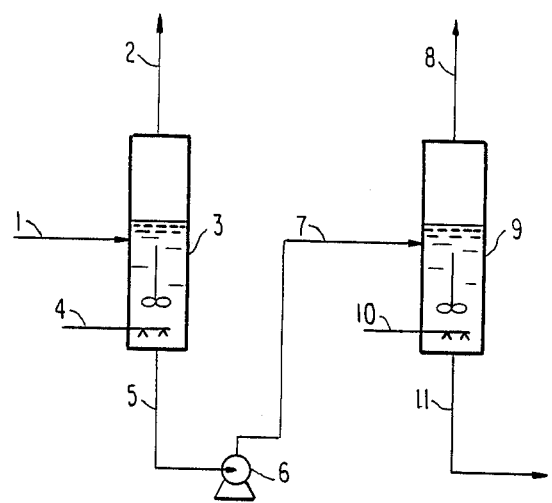

PROCESS FOR PREPARING BENZOPHENONE-AZINES

This is a continuation of application Ser. No. 702,551, filed 2/19/85, now abandoned.

FIELD OF THE INVENTION

This invention relates to a process for preparing benzophenone-azines by oxidation of benzophenone-imines with molecular oxygen in the presence of a copper halide catalyst.

BACKGROUND OF THE INVENTION

Processes for preparing benzophenone-azines by oxidation of corresponding benzophenone-imines are conventionally known as disclosed, e.g., in U.S. Pat. No. 2,870,206 in which benzophenone-imines are contacted with molecular oxygen to produce benzophenone-azines. However, these conventional processes have technical and economical problems awaiting solution and have not yet been carried out on a large commercial scale. A particularly serious technical problem is insolubilization and sedimentation of the catalyst during the reaction, which causes various disadvantages such that: (1) the reaction rate decreases due to inactivation of the catalyst; (2) the sedimented copper salt is highly corrosive to corrode apparatuses; (3) the sedimented copper salt attaches to the wall of the reactor or pipe line, resulting in reduction of heat transfer efficiency or obstruction of the pass; (4) side reactions are induced; (5) the rate of recovery of the catalyst from the reaction mixture is reduced; and the like. These phenomena not only are disadvantageous in a batchwise reaction system but give rise to a momentous problem for stable operation particularly in a continuous reaction system.

The present inventors have conducted extensive investigations on a continuous process for preparing benzophenone-azines that can be effected on an industrial scale without involving the above-described disadvantages and, as a result, found that insolubilization of copper salt catalysts is primarily influenced by water present in the reaction system and can be suppressed by maintaining the water concentration in the reaction mixture at 1,000 ppm or less during the reaction in a continuous system [Japanese Patent Application (OPI) No. 103816/79 (the term "OPI" as used herein means an "unexamined published patent application")]. Several possible methods are considered in order to remove produced water from the reaction mixture to control the water concentration. From the standpoint of avoiding adverse influences on the reaction system and workability, the most practical process comprises introducing more oxygen or oxygen-containing gases than necessary for the oxidation reaction whereby produced water is driven out of the system together with the excessive oxygen. It is necessary to increase the amount of the gas to be introduced in order to ensure a further lowered water concentration. On the other hand, the oxidation reaction rate of benzophenone-imines depends on the oxygen partial pressure. Therefore, if in using inexpensive air as an oxygen-containing gas, the reaction is advantageously performed under pressure for attaining an industrially practical reaction rate in view of the low oxygen level in air. However, the so increased pressure rises the partial pressure of water even if the water concentration in the gaseous phase in the reaction system is low, thus resulting in rise of the water concentration in the liquid phase. Therefore, to elevate the reaction pressure requires increase of the amount of the gas to be introduced as compared with the reaction under a low pressure, which entails increase of cost of power.

SUMMARY OF THE INVENTION

As a result of further investigations, it has now been found that produced water accelerates sedimentation of the copper salt catalyst but such an influence of water is small when the molar ratio of the benzophenone-imines to the copper halide in the reaction mixture is high, while it becomes greater as the molar ratio decreases and that the molar ratio of less than 1 seriously deteriorates solution stability of copper halide and is likely to induce sedimentation of the copper halide.

The present invention provides a process for continuously preparing benzophenone-azines by oxidizing benzophenone-imines with molecular oxygen or an oxygen-containing gas in the presence of a copper halide catalyst, wherein the reaction is carried out in a multi-stage system under an oxygen partial pressure gradually decreasing from the former stage to the latter stage and at a conversion gradually decreasing from the former stage to the latter stage, while controlling the conversion so that the molar ratio of benzophenone-imines to the copper halide in the final stage be maintained at 1 or more.

According to the process of this invention, since the former stage having a higher ratio of the benzophenone-imines to the copper halide catalyst has a higher permissible water concentration of the reaction mixture or a higher permissible water partial pressure of the gaseous phase, it is possible to conduct the reaction under pressure, or to conduct the reaction at a high reaction rate by raising the oxygen concentration in the introduced gas. Further, the reaction can be effected using a small-sized reactor. Furthermore, since the permissible water concentration in the reaction mixture is high, the amount of the gas to be introduced for removal of water needs not be so increased.

To the contrary, in the latter stage in which conversion of the benzophenone-imines has proceeded to a certain extent, the molar ratio of the benzophenone-imines to the copper halide and the permissible water partial pressure become smaller. Therefore, the reaction is effected at a rate lower than that of the former stage by reducing the reaction pressure or the oxygen concentration of the introduced gas. The water partial pressure can easily be fallen below the permissible level with a small amount of gas introduced. The reaction rate does not depend on the concentration of benzophenone-imines and becomes lower towards the latter stages by reducing the oxygen partial pressure. The reduction of the reaction rate in the latter stage does not give rise to a serious barrier if a high conversion of benzophenone-imine is provided in the former stage wherein the catalyst has high solubility.

In the present invention, the reaction is carried out in multistage wherein the conversion of imines (on the basis of benzophenone-imines introduced into the first stage) is higher in the former stage than in the latter stage, preferably in such a manner that the conversion in the final stage is from 5 to 30%.

Further, the copper halide is apt to get sedimented if the molar ratio of the imine to the copper halide is less than 1 as described above. Therefore, conversion of the benzophenone-imines should be stopped before the benzophenone-imines/copper halide molar ratio falls down to less than 1. It is preferable that the benzophenone-imines/copper halide molar ratio be adjusted to 1 to 5, and preferably 1 to 3, in the final stage and 2 to 20, and preferably 3 to 10, in the stages before the final stage.

The process of the present invention overcomes various disadvantages resulting from insolubilization and sedimentation of the catalyst, thus making it possible not only to achieve stable continuous reaction at a high conversion of benzophenone-imines but also to reduce the requisite amount of the gas to be introduced. In addition, the process of the present invention eliminates the necessity to use a large-sized apparatus.

Thus, the present invention provides an economically advantageous process for preparing benzophenone-azines which can eliminate various disadvantages associated with the impractical conventional processes.

BRIEF DESCRIPTION OF THE DRAWING

FIGURE is a flow sheet of the reaction in Example 1. The elements are: supply pipe for benzophenone-imines 1, pipes for discharging air 2 and 8, first reactor 3, pipes for introducing air 4 and 10, pipes for discharging reaction solution 5 to 11, pump 6, pipe for introducing reaction solution 7, and second reactor 9.

DETAILED DESCRIPTION OF THE INVENTION

The benzophenone-imines which can be used in the present invention can be represented by the formula (I):

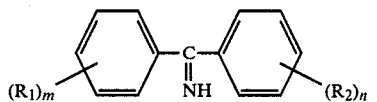

wherein $R_1$ and $R_2$, which may be the same or different, each represents an acyclic, alicyclic or aromatic hydrocarbon group having from 1 to 10 carbon atoms, an ether, acyl, acyloxy, alkoxycarbonyl, carboxylic acid amido or di-substituted amino group derived from these hydrocarbon groups, a halogen atom, a hydroxyl group, a nitro group or a cyano group, or $R_1$ and $R_2$ may be taken together to form a single bond or a ring; and m and n each represents 0 or an integer of from 1 to 5.

Specific examples of the benzophenone-imines represented by the formula (I) include benzophenone-imine, 2-, 3- or 4-methylbenzphenone-imine, 2-, 3- or 4-ethylbenzophenone-imine, 2-, 3- or 4-n- and/or isopropylbenzophenone-imine, 2-, 3- or 4-n- and/or iso- and/or tert-butylbenzophenone-imine, 2-, 3- or 4-amylbenzophenone-imine, 2-, 3- or 4-decylbenzophenone-imine, 2-, 3- or 4-methoxybenzophenone-imine, 4-cyclohexylbenzophenone-imine, 4-phenylbenzophenone-imine, 2,4-dimethylbenzophenone-imine, 2,3-dimethylbenzophenone-imine, 3,4-dimethylbenzophenone-imine, 2,4-diethylbenzophenone-imine, 2,3-diethylbenzophenone-imine, 3,4-diethylbenzophenone-imine, 2-methyl-4-ethylbenzophenone-imine, 2-methyl-4-butylbenzophenone-imine, 2,2'-, 3,3'-, 4,4'-, 2,3'-, 2,4'- or 3,4'-dimethylbenzophenone-imine, 2-, 3- or 4-chlorobenzophenone-imine, 2-chloro-4-methylbenzophenone-imine, 4-chloro-4'-methylbenzophenone-imine, 4,4'-dichlorobenzophenone-imine, 4-nitrobenzophenone-imine, 2,4-dinitrobenzophenone-imine, 4-hydroxybenzophenone-imine, 4-N,N-dimethylaminobenzophenone-imine, 4-acetylbenzophenone-imine, 4-methoxybenzophenone-imine, 4-N,N-dimethylcarbamoylbenzophenone-imine, 4-cyanobenzophenone-imine, fluorenone-imine, xanthone-imine, anthrone-imine, acridone-imine, and the like.

The imine compounds which can be used in the present invention have been illustrated with reference to their specific examples, but, as a matter of course, other imine compounds may also be used.

Methods for preparing these and other imines include, for example, a method of reacting a corresponding benzophenones with ammonia, a method of reacting benzonitriles with an aryl magnesium bromide, i.e., a Grignard reagent, a method of dehydrating a diarylamine alcohol, and the like. All imines prepared by any of these methods can be employed in the present invention.

The benzophenone-imines that can be used in the present invention except for unsubstituted benzophenone-imine of the formula (I) wherein m and n are 0 are those containing various substituents or with substituents jointly forming a single bond or a ring. In carrying out the process of the invention on an industrial scale, unsubstituted benzophenone-imine and 1- or 2-mono- or 1,2-di-substituted benzophenone-imine are preferred. Among them, unsubstituted benzophenone-imine is particularly preferred.

The copper halide which can be used as a catalyst in the process of this invention preferably includes cuprous chloride, cuprous bromide and cuprous iodide, with cuprous chloride being more preferred.

Solvents are not particularly required in the present invention. It is possible, however, to use solvents for the purpose of helping dissolution of the produced benzophenone-azines and maintaining the reaction system in a solution state. Such being the case, solvents that are not oxidized in the ammoxydation of benzophenones of oxidation of benzophenone-imines and promote dissolution of benzophenone-azines and, in particular, have poor miscibility with water and a low viscosity are preferred. Examples of such solvents are benzene, toluene, o-, m- or p-xylene, ethylbenzene, mesitylene, cumene, pseudocumene, amylbenzene, aromatic hydrocarbons having from 6 to 16 carbon atoms, chlorobenzene, o-, m- or p-dichlorobenzene, nitrobenzene, o-, m- or p-dinitrobenzene, o-, m- or p-chlorotoluene, diphenyl, phenanthrene, anisole, diphenyl ether, acetophenone, dibenzyl, benzophenone, hexane, heptane, cyclohexane, cyclooctane, ethylcyclohexane, ethylene dichloride, tetrachloroethylene, diisopropyl ether, diisopropyl ether, diisobutyl ketone, butyl acetate, butyl benzoate, phenyl benzoate, dimethyl phthalate, and the like. Of these, benzphene is most preferred. It is usually preferable to use an imination reaction mixture of benzophenones as the starting benzophenone-imines. In case of using the imination reaction mixture, a solvent is not always necessary since the unreacted benzophenone remaining in the reaction mixture serves as a solvent.

The term "multistage reaction system" as used herein means a reaction system composed of two or more reaction chambers through which the oxidation reaction mixture successively passes and each of which maintains a different oxygen pressure. Such a reaction system may comprise a plurality of reaction vessels connected in a series, or a plurality of reaction chambers united in one column. The number of stages is not particularly restricted as long as it is two or more, but too many stages make operation complicated. Usually, two or three stages, and preferably two stages, are employed.

The reaction temperature ranges from 60° to 300° C., preferably from 70° to 250° C., and more preferably from 90° to 230° C. The reaction temperature in each reaction stage may be the same or different.

The reaction time cannot be definitely specified since it varies depending upon the amount of the catalyst, the partial pressure of oxygen, etc., but is usually in the range of from 0.1 to several tens hours. The reaction time for each stage may be the same or different.

Large amounts of the copper halide catalyst bring about high reaction rates but in order to control the molar ratio of benzophenone-imine to copper halide within the above-recited range of from 1 to 5 in the final stage, the finally achieved conversion of benzophenone-imines has to be lowered. In turn, small amounts of the catalyst reduce the reaction rate. Accordingly, the amount of the copper halide catalyst to be used should be determined taking into account the factors giving influences on the reaction rate, such as temperature, partial oxygen pressure, reaction time, and the like, and usually ranges from 500 to 5,000 ppm as a Cu concentration in the reaction mixture.

Molecular oxygen may include pure oxygen and a mixed gas comprising oxygen and an inert gas, e.g., nitrogen, namely air. According to the present invention, the partial oxygen pressure is lower in the latter stage than in the former stage within such a range that the oxygen partial pressure in the final stage is from 0.1 to 1 atm. and from 0.3 to 10 atm. in the former stage or stages.

Oxygen or an oxygen-containing mixed gas is continuously introduced into the reaction system, which is preferably dried.

The amount of gas to be introduced should be large enough such that the partial water pressure in each reaction stage should be less than the permissible level in agreement with the benzophenone-imines/copper halide molar ratio of the respective reaction stage. Such an amount varies depending on the reaction temperature, total pressure, oxygen partial pressure, catalyst concentration, retension time, benzophenone-imines/copper halide molar ratio and the like and, therefore, cannot be definitely determined. In the present invention, however, the total requisite amount of oxygen or an oxygen-containing gas can be greatly lessened as compared with one-step reaction since a continuous reaction ca be effected in a multistage system in which different reaction conditions can be applied in conformity with the conversion of benzophenone-imines, i.e., the benzophenone-imines/copper halide molar ratio.

The present invention will now be illustrated in greater detail with reference to an example and comparative examples, but it should be understood that the present invention is not limited thereto. In these examples, all percents are given by weight unless otherwise indicated.

EXAMPLE

Benzophenone-azine was produced using the apparatus as shown in FIGURE.

In each of 2-liter reactors (3) and (9) each equipped with a gas sparger and stirring wings was charged 1,000 g of benzophenone-imine solution (benzophenone-imine: 25.0%; CuCl: 0.4%; the remainder was benzophenone) as a raw material. The reaction was continuously carried out in the two reactors at 120° C. and at 4 Kg/cm²G in reactor (3) and 0 Kg/cm²G in reactor (9).

Benzophenone-imine was supplied into reactor (3) through pipe (1) at a rate of 500 g/hr, and air was supplied into reactor (3) through pipe (4) at a rate of 0.85 Nl/min. The reaction mixture was withdrawn from pipe (5). The reaction was continuously carried out so that the raw material resides in reactor (3) for 2 hours in average.

The reaction mixture discharged from reactor (3) was supplied into reactor (9) through pipe (7), and air was supplied therein through pipe (10) at a rate of 0.11 Nl/min. The reaction mixture was discharged through pipe (11). The reaction was continuously carried out so that the raw material resides in reactor (9) for 2 hours. After 48-hour continuous reaction, the reaction mixture discharged from pipe (5) contained 3.8% of benzophenone-imine and 21.2% of benzophenone-azine (yield: 85%) and had a benzophenone-imine/copper molar ratio of 5.0. The reaction mixture discharged from pipe (11) contained 0.9% of benzophenone-imine and 24.2% of benzophenone-azine (yield: 96%) and had a benzophenone-imine/copper molar ratio of 1.2. The water concentrations at pipes for discharging air (2) and (8) were 12 mol% and 13 mol%, respectively.

The resulting mixture was a clear reddish brown solution, and no sedimentation of copper chloride was observed in either of reactors (3) and (9).

COMPARATIVE EXAMPLE 1

The reaction was carried out using only reactor (3) at a pressure of 4 Kg/cm²G.

The same procedure as described in Example 1 was repeated except that 2,000 g of the starting benzophenone-imine solution was charged in reactor (3) and retained therein for 4 hours in average while introducing air at a rate of 1.40 Nl/min.

After 48-hour continuous reaction, the reaction mixture withdrawn through pipe (5) contained 2.3% of benzophenone-imine and 22.5% of benzophenone-azine (yield: 90%) and had a benzophenone-imine/copper molar ratio of 3.1. The water concentration in the pipe (2) was 8.0 mol%.

The resulting reaction mixture was opaque and greenish black. Sedimentation of the catalyst was observed in reactor (3), and a part of the sedimented catalyst attached to the wall of reactor (3).

COMPARATIVE EXAMPLE 2

The reaction was continuously conducted using only reactor (3) having a volume of 10 liters at a pressure of 0 Kg/cm²G.

The same procedure as described in Example 1 was repeated except that 5,000 g of the starting benzophenone-imine solution was charged in reactor (3) and retained therein for 10 hours in average while supplying air at a rate of 1.0 Nl/min.

After 48-hour continuous reaction, the reaction mixture from pipe (5) contained 1.2% of benzophenone-imine and 23.8% of benzophenone-azine (yield: 95%) and had an imine/copper molar ratio of 1.6. The water concentration in pipe (2) was 12%. The resulting reaction mixture was a clear reddish brown solution. No sedimentation of the catalyst was observed, but the reaction required a long time and a large-sized reactor.

COMPARATIVE EXAMPLE 3

The reaction was continuously performed using only reactor (3) having a volume of 4 liters at a pressure of 0 Kg/cm$^2$G.

The same procedure as described in Example 1 was repeated except that 2000 g of the starting benzophenone-imine solution was charged in the reactor and retained therein for 4 hours in average while introducing air at a rate of 1.0 Nl/min.

After the reaction was continued for 48 hours, the reaction mixture withdrawn from pipe (5) contained 15.5% of benzophenone-imine and 9.5% of benzophenone-azine (yield: 38%) and had an imine/copper molar ratio of 21.2. The water concentration in pipe (2) was 4.8 mol%. The resulting reaction mixture was a clear reddish brown solution, and no sedimentation of the catalyst was observed.

While the invention has been described in detail and with reference to specific embodiments thereof, it will be apparent to one skilled in the art that various changes and modifications can be made therein without departing from the spirit and scope thereof.

What is claimed is:

1. A process for continuously preparing benzophenone-azines comprising oxidizing benzophenone-imines with molecular oxygen or a molecular oxygen-containing gas in the presence of a copper halide catalyst, wherein the oxidation reaction is carried out in a multi-stage system under an oxygen partial pressure decreasing from the former stage to the latter stage and at a conversion gradually decreasing from the former stage to the latter stage, while controlling the conversion so that the molar ratio of the benzophenone-imines to the copper halide in the final stage be maintained at from 1 to 3, wherein the partial pressure of oxygen is lower in the latter stage than in the former stage within such a range that the partial pressure of oxygen in the final stage is from 0.1 to 1 atm and that in the former stage or stages is from 0.3 to 10 atm, and wherein the conversion in the final stage is from 5 to 30% and wherein the molar ratio of the benzophenone-imines to the copper halide in the former stage or stages is from 2 to 20.

2. A process as claimed in claim 1, wherein the multi-stage system comprises 2 or 3 stages.

3. A process as claimed in claim 1, wherein the multi-stage system comprises 2 stages.

4. A process as claimed in claim 1, wherein the benzophenone-imines is benzophenone-imine.

5. A process as claimed in claim 1, wherein the copper halide is cuprous chloride.

6. A process as claimed in claim 1, wherein the reaction is carried out in the presence of benzophenone as a solvent.

7. A process as claimed in claim 1, wherein the reaction is carried out at a temperature of from 60° to 300° C.

8. A process as claimed in claim 1, wherein the reaction is carried out at a temperature of from 70° to 250° C.

9. A process as claimed in claim 1, wherein the reaction is carried out at a temperature of from 90° to 230° C.

10. A process as claimed in claim 1, wherein the copper halide is present in an amount of from 500 to 5,000 ppm as Cu metal concentration in the reaction mixture.

11. A process as claimed in claim 1, wherein the molar ratio of the benzophenone-imines to the copper halide in the final stage is from 1 to 3 and that in the former stage or stages is from 3 to 10.

* * * * *